United States Patent [19]

Boell

[11] 4,335,241
[45] Jun. 15, 1982

[54] 4-α-AMINO-ARYLMETHYL-6-METHYL-1,3-DIHYDRO-FURO[3,4-c]PYRIDIN-7-OLS

[75] Inventor: Walter Boell, Dannstadt-Schauernheim, Fed. Rep. of Germany

[73] Assignee: BASF Aktiengesellschaft, Fed. Rep. of Germany

[21] Appl. No.: 236,904

[22] Filed: Feb. 23, 1981

[30] Foreign Application Priority Data

Mar. 6, 1980 [DE] Fed. Rep. of Germany ....... 3008522

[51] Int. Cl.³ .......................................... C07D 491/048
[52] U.S. Cl. ..................... 544/127; 544/362; 546/116; 260/244.4
[58] Field of Search ..................... 546/116; 260/244.4; 544/127, 362

[56] References Cited

U.S. PATENT DOCUMENTS 4,168,379 9/1979 Boell et al. ............................ 546/116
4,206,117 6/1980 Von Philipsborn et al. ......... 546/116

FOREIGN PATENT DOCUMENTS 2711655 9/1978 Fed. Rep. of Germany ...... 546/116

OTHER PUBLICATIONS

Yamada et al., Tetrahedron Letters, 1979, pp. 2603–2606.

Stempel et al., Jour. Amer. Chem. Soc. 71, 1949, pp. 2969–2972.

Dejardin et al., Bull. Soc. Chim. France II, 1978, pp. 75–82.

Primary Examiner—Jane T. Fan
Attorney, Agent, or Firm—Keil & Witherspoon

[57] ABSTRACT

4-α-Amino-arylmethyl-6-methyl-1,3-dihydro-furo[3,4-c]pyridin-7-ols of the formula

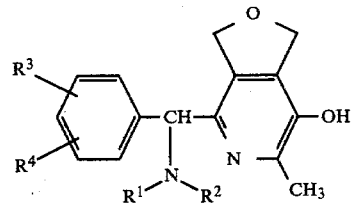

where
$R^1$ and $R^2$ together are alkylene which may be interrupted by a hetero-atom and may be substituted by $C_{1-4}$-alkyl, and
$R^3$ and $R^4$ are hydrogen, hydroxyl, $C_{1-3}$-alkyl, $C_{1-3}$-alkoxy or halogen, processes for their preparation, and their use for the preparation of pyridinyl aminoalkyl ethers.

1 Claim, No Drawings

4-α-AMINO-ARYLMETHYL-6-METHYL-1,3-DIHYDRO-FURO[3,4-c]PYRIDIN-7-OLS

The present invention relates to 4-α-aminoarylmethyl-6-methyl-1,3-dihydro-furo[3,4-c]pyridin-7-ols, processes for their preparation, and their use for the preparation of pyridinyl aminoalkyl ethers.

Pyridinyl aminoalkyl ethers of the formula IV

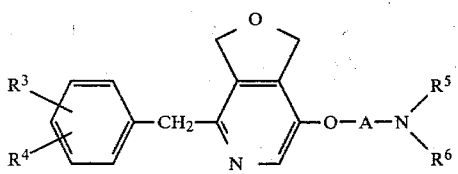

where
R$^3$ and R$^4$ are hydrogen, hydroxyl, C$_{1-3}$-alkyl, C$_{1-3}$-alkoxy or halogen,
R$^5$ is hydrogen or C$_{1-6}$-alkyl, which may be substituted by hydroxyl, C$_{1-4}$-alkoxy, C$_{1-4}$-alkylthio, C$_{1-4}$-alkylamino or di-C$_{1-4}$-alkylamino or by phenoxy or phenyl which are unsubstituted or substituted by C$_{1-3}$-alkyl or C$_{1-3}$-alkoxy, or is C$_{3-6}$-alkenyl, C$_{3-6}$-alkynyl or C$_{3-8}$-cycloalkyl, which may be substituted by C$_{1-3}$-alkyl or by phenyl which is unsubstituted or substituted by C$_{1-3}$-alkyl or C$_{1-3}$-alkoxy,
R$^6$ is hydrogen or C$_{1-6}$-alkyl or
R$^5$ and R$^6$ together with an N atom are a 4-membered to 8-membered ring which may contain an oxygen atom, a sulfur atom or a further nitrogen atom, and may be substituted by C$_{1-3}$-alkyl, C$_{3-8}$-cycloalkyl, hydroxyl, C$_{1-4}$-alkoxy or phenyl or phenyl-C$_{1-3}$-alkyl which are unsubstituted or are substituted by C$_{1-3}$-alkyl or C$_{1-3}$-alkoxy, and
A is C$_{2-8}$-alkylene which is saturated or unsaturated and unsubstituted or substituted by hydroxyl, are disclosed as anti-arrhythmically active compounds in German Laid-Open Application DOS 2,711,655. They are prepared from oxazoles and olefins, the pyridinols first obtained being then reacted with an alkylating agent. This process is very laborious because the oxazoles required as starting materials are difficult to obtain.

I have now found novel intermediates from which pyridinyl aminoalkyl ethers may be prepared in a simple manner.

The present invention relates to 4-α-aminoarylmethyl-6-methyl-1,3-dihydro-furo[3,4-c]pyridin-7-ols of the formula I

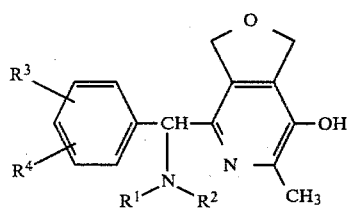

where
R$^1$ and R$^2$ together are alkylene which may be interrupted by a hetero-atom and may be substituted by a C$_{1-4}$-alkyl, and
R$^3$ and R$^4$ have the same meanings as above.

The invention further relates to a process for the preparation of the compounds of the formula I, wherein a 6-methyl-1,3-dihydro-furo[3,4-c]pyridin-7-ol VI is reacted with an aldehyde of the formula II

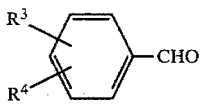

where R$^3$ and R$^4$ have the same meanings as above, and a cyclic amine of the formula III $$HNR^1R^2 \qquad (III)$$

where R$^1$ and R$^2$ have the same meanings as above.

Finally, the invention also relates to a process for the preparation of compounds of the formula IV, wherein the cycloamino group —NR$^1$R$^2$ in a compound of the formula I is eliminated by hydrogenation and thereafter the group of the formula V

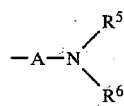

where A, R$^5$ and R$^6$ have the same meanings as above, is introduced into the reaction product.

The reaction of II with III is a Mannich reaction. There are only few methods by means of which a substituent can be introduced into the 6-position of a pyridoxine system. In addition to the method described in German Laid-Open Application DOS No. 2,711,655, there is also a very recently published process (Y. Yamada et al., Tetrah. Letters 1979, 2603), but this does not lead to the desired compounds. A Mannich reaction with unsubstituted pyridin-3-ol or with a pyridin-3-ol having a low degree of substitution has been disclosed, but gives the 2-substituted derivatives. Substitution of the 6-position is difficult or impossible to achieve (A. Stempel and E. C. Buzzi, J. Amer. Chem. Soc. 71, 2969 (1949); J. V. Dejardin and C. L. Lapiere, Bull. Soc. chim. France II 1978, 75). It was therefore surprising and not foreseeable that in the case of a highly substituted compound of type I the reaction described would prove feasible. The fact that non-cyclic amines such as dipropylamine, diisobutylamine, N-methylaniline or benzylamine give only minor amounts, if any, of the desired compound shows that the reaction is highly sensitive to the particular conditions.

Two methods have proved useful for carrying out the reaction, namely reaction of all the components simultaneously (method A) or preliminary preparation of the aminal from the amine and the aldehyde, and separate reaction thereof with VI (method B); in all cases, it is advantageous to use a less than equivalent amount of VI, as this is the most expensive component. The reaction may be carried out in a solvent (toluene, chlorobenzene, dimethylformamide, dimethylsulfoxide or 1,2-diethoxyethane) or in the absence of a solvent (in which case it is advantageous to use a greater excess of the amine). The reaction temperature should be from 80° to 150° C.

Preferred cyclic amines are piperidine, 3-methylpiperidine, 4-methylpiperidine, morpholine, 3-methylmorpholine, piperazine, N-methyl-piperazine, hexamethyleneimine, pyrrolidine, 3-methylpyrrolidine, 1,3-propyleneimine and ethyleneimine.

In converting I to IV, the radical $NR^1R^2$ is first eliminated hydrogenolytically in a conventional manner (cf. P. N. Rylander: Catalytic Hydrogenation in Organic Syntheses, Academic Press, New York 1979, pages 280–284). The catalyst used is palladium, platinum, nickel chromite or copper chromite. The preferred conditions are the use of 5–10% strength palladium on active charcoal, under a hydrogen pressure of up to 50 bar, and at a reaction temperature of 0°–60° C. Conventional solvents are esters and alcohols.

The reaction of the resulting compound with V is described in detail in German Laid-Open Application DOS No. 2,711,655 (cf. pages 7–9).

By means of the invention it is possible to use, as the starting material for the synthesis of IV, the easily obtainable compound pyridoxine (vitamin $B_6$), which can be converted to 6-methyl-1,3-dihydro-furo[3,4]pyridin-7-ol VI by treatment with acid (cf. J. Amer. Chem. Soc. 61 (1939), 3307).

VI is an inner ether of pyridoxine (vitamin $B_6$) and has the following structure:

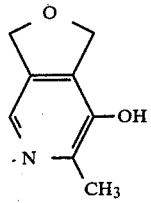 (VI)

EXAMPLE 1

(Preparation of I, method A)

(a) Preparation of the starting material 50 g of pyridoxine hydrochloride (0.24 mole) are introduced into a mixture of 11 ml of concentrated hydrochloric acid and 9 ml of water in a 100 ml enamelled autoclave. The mixture is heated for 10 hours at 150° C. and is then allowed to cool to about 40° C., and the crystals are filtered off and washed with 6 ml of ethanol. After drying at 100° C. under 20 mbar, 27.0 g of 6-methyl-1,3-dihydro-furo[3,4-c]pyridin-7-ol hydrochloride are obtained; melting point 240°–241° C.

(b) Preparation of the end product 200 g of morpholine are introduced, under nitrogen, into a 1 liter four-neck flask equipped with a stirrer, reflux condenser, thermometer and dropping funnel. 75 g (0.4 mole) of the product obtained according to (a) are introduced, while stirring, 64 g (0.6 mole) of benzaldehyde are run in, causing the internal temperature to rise to 95° C., and the mixture is then heated for 2.5 hours at 125°–130° C. Morpholine is then stripped off at 90°–100° C. under reduced pressure (down to 25 mbar). The viscous mixture is cooled to 70° C., and 200 ml of methylene chloride are added slowly, after which a solution of 66 g (1 mole) of 85% pure potassium hydroxide in 400 ml of water is introduced, whilst cooling at 20° C. The two phases are stirred vigorously for 5 minutes and are then separated, and the aqueous alkaline phase is again extracted, using 100 ml of methylene chloride. The organic phases are disclosed. The combined aqueous solutions are brought to pH 8–9 with 200 ml of a 1:3 dilution of concentrated hydrochloric acid. This addition of acid causes an oil to separate out. After separating the phases, the aqueous solution is extracted once more, with 100 ml of methylene chloride. The methylene chloride solution is concentrated on a rotary evaporator, and the residue (149 g) together with the oil is recrystallized from 450 ml of isopropanol. The ice-cooled, easily stirrable suspension of the crystals is filtered, and the filter residue is washed with a small amount of isopropanol. After drying under greatly reduced pressure at 60° C., 141 g of 4-(α-N-morpholino)-benzyl-6-methyl-1,3-dihydro-furo[3,4-c]pyridin-7-ol are obtained; melting point 83°–85° C. According to the NMR spectrum and elementary analysis, the product contains 2 moles of isopropanol per mole of pyridinol; it is pure according to thin layer chromatography (silica gel, ethyl acetate + 15% of methanol). Yield 79%.

EXAMPLE 2

(Preparation of I, method B)

34.1 g (0.4 mole) of piperidine are added dropwise to 21.2 g (0.2 mole) of benzaldehyde, whilst cooling to keep the mixture below 35° C. The solidified product is recrystallized from acetone. After drying, 33.4 g of benzaldehyde dipiperidinyl-aminal are obtained; melting point 80°–81° C.

A mixture of 26 g (100 mmoles) of benzaldehyde dipiperidinyl-aminal and 12.1 g (80 mmoles) of 6-methyl-1,3-dihydro-furo[3,4-c]pyridin-7-ol in 60 ml of dimethylformamide is heated for 4 hours at 110° C. The volatile material is distilled off at 70° C./1.3 mbar. Chromatography of the residue over silica gel (methylene chloride/ethyl acetate) and recrystallization from acetone gives 13.0 g of 4-(α-N-piperidino)-benzyl-6-methyl-1,3-dihydro-furo[3,4-c]pyridin-7-ol; melting point 169°–170° C.; yield 50%.

The following substances are obtained similarly:

| Example | $R^3$ | $R^4$ | $N\diagdown{R^4 \atop R^5}$ | Method of preparation | Yield[1] | Melting point |
|---|---|---|---|---|---|---|
| 3 | H | H | Piperidine | A | 56% | 167–168° C. |
| 4 | H | H | Pyrrolidine | A | 48% | 204–206° C.[2] |
| 5 | 4-CH₃ | H | Piperidine | A | 38% | 202–204° C.[2] |
| 6 | 4-Cl | H | Piperidine | A | 34% | 198–200° C.[3] |
| 7 | 3-CH₃O | 4-CH₃O | Morpholine | A | 49% | 172–173° C.[3] |

[1]Product of sufficient purity for the hydrogenolysis stage
[2]As the mono-hydrochloride
[3]As the bis-hydrochloride

EXAMPLE 8

Preparation of 4-benzyl-6-methyl-1,3-dihydro-furo[3,4-c]pyridin-7-yl 3-isopropylaminopropyl ether (cf. formula IV)

1st Stage 67.5 g (150 mmoles) of 4-(α-N-morpholino)-benzyl-6-methyl-1,3-dihydro-furo[3,4-c]pyridin-7-ol and 300 mmoles of isopropanol in 220 ml of methanol are hydrogenated, after addition of 1.5 g of 10% strength Pd/C, under 10 bar hydrogen pressure, in an 0.5 liter stirred autoclave. Hydrogen is absorbed for about 12 hours and the temperature rises to 35° C.

After 18 hours, the pressure is released and the autoclave is flushed with nitrogen. Sodium hydroxide solution (6.6 g = 165 mmoles of NaOH in 47 ml of water) is added, the mixture is stirred for 20 minutes, and the catalyst is filtered off and washed with a small amount of water. The filtrate (pH 12.8) is brought to pH 9 with ⅓ concentrated hydrochloric acid, whereupon the product precipitates. It is filtered off at 10° C., washed with 120 ml of water, and dried at 80° C./3 mbar, giving 34.0 g of 4-benzyl-6-methyl-1,3-dihydro-furo[3,4-c]pyridin-7-ol, melting point 218°–219° C.; yield 94%.

2nd Stage (a) A mixture of 24.2 g (100 mmoles) of 4-benzyl-6-methyl-1,3-dihydro-furo[3,4-c]pyridin-7-ol, 113 g (1 mole) of 1,3-dichloropropane, 2 g of benzyltriethylammonium chloride, 100 ml of toluene and 100 g of 50% strength sodium hydroxide solution is heated for 3 hours at 90° C., whilst stirring. The organic phase is separated off and washed with 50 ml of water. After stripping off the solvent and the excess 1,3-dichloropropane, 30.7 g of 4-benzyl-6-methyl-1,3-dihydrofuro[3,4-c]pyridin-7-yl 3-chloropropyl ether remain, containing a small amount of 1,3-bis-(4-benzyl-6-methyl-1,3-dihydro-furo[3,4-c]pyridin-7-oxy)-propane which does not interfere with the subsequent reaction.

(b) A mixture of 24.2 g (100 mmoles) of 4-benzyl-6-methyl-1,3-dihydro-furo[3,4-c]pyridin-7-ol, 226 g (2 moles) of 1,3-dichloropropane, 2 g of benzyltriethylammonium chloride and 100 g of 50% strength sodium hydroxide solution is heated for 3 hours at 90° C., while stirring. The organic phase is separated off and washed with 50 ml of water. After stripping off the excess 1,3-dichloropropane, 30.7 g of 4-benzyl-6-methyl-1,3-dihydro-furo[3,4-c]pyridin-7-yl 3-chloropropyl ether remain, containing a small amount of 1,3-bis-(4-benzyl-6-methyl-1,3-dihydro-furo[3,4-c]pyridin-7-oxy)-propane which does not interefere with the subsequent reaction.

(c) 24.2 g (100 mmoles) of 4-benzyl-6-methyl-1,3-dihydro-furo[3,4-c]pyridin-7-ol are suspended in 80 ml of dry dimethylsulfoxide and converted to the sodium salt by adding 3.5 g (120 mmoles) of sodium hydride (85% strength in oil) at 20° C. When the evolution of hydrogen has ceased, 113 g (1 mole) of 1,3-dichloropropane are added dropwise at 0°–10° C. and the mixture is stirred for 15 hours at 20° C. The dimethylsulfoxide and the excess 1,3-dichloropropane are distilled off under greatly reduced pressure. The residue is taken up in 250 ml of methylene chloride and this solution is extracted twice with 50 ml of 10% strength sodium hydroxide solution and is washed with 10 ml of water. After distilling off the solvent, 30.7 g of 4-benzyl-6-methyl-1,3-dihydro-furo[3,4-c]pyridin-7-yl-3-chloropropyl ether, containing a small amount of 1,3-bis-(4-benzyl-6-methyl-1,3-dihydro-furo[3,4-c]pyridin-7-oxy)-propane, remain.

3rd Stage 8.0 g (25 mmoles) of the product obtained according to (a), (b) or (c) and 15 g (250 mmoles) of isopropylamine are heated for 7 hours in an autoclave at 100° C. The excess amine is distilled off under reduced pressure. The residue is purified by chromatography over silica gel (using ethyl acetate and methanol). The resulting 4-benzyl-6-methyl-1,3-dihydro-furo[3,4-c]pyridin-7-yl 3-isopropylaminopropyl ether is converted, by means of dilute hydrochloric acid, into the bis-hydrochloride, which is recrystallized from isopropanol; 7.8 g, of melting point 162° C., are obtained.

The crude product can also be purified by extraction with dilute hydrochloric acid instead of by chromatography. For this purpose, 1 N hydrochloric acid is added to a shaken solution of the crude product in toluene, until the aqueous phase has a pH of 6.7. On separating off and concentrating the aqueous phase, 4-benzyl-6-methyl-1,3-dihydro-furo[3,4-c]pyridin-7-yl 3-isopropylaminopropyl ether is obtained as the monohydrochloride, whilst the less basic impurities remain in the toluene phase.

EXAMPLE 9

12.1 g (50 mmoles) of 4-benzyl-6-methyl-1,3-dihydro-furo[3,4-c]pyridin-7-ol (compare Example 8, stage 1) are suspended in 40 ml of dry dimethylsulfoxide and converted to the sodium salt by adding 1.75 g (60 mmoles) of sodium hydride (85% strength in oil) at 20° C. When the evolution of hydrogen has ceased, 8.1 g (75 mmoles) of freshly distilled β-dimethylaminoethyl chloride are added dropwise, and the mixture is left to stand for 15 hours at 10° C. The dimethylsulfoxide is then distilled off under greatly reduced pressure. The residue is taken up in methylene chloride, the salts and the unconverted pyridinol are washed out with dilute sodium hydroxide solution and the organic phase is dried and concentrated under reduced pressure. The residue is converted, by means of dilute hydrochloric acid, into the hydrochloride, which is recrystallized from an ethanol/ether mixture. 10.0 g of 4-benzyl-6-methyl-1,3-dihydro-furo[3,4-c]pyridin-7-yl β-dimethylaminoethyl ether bis-hydrochloride, of melting point 213°–214° C., are obtained.

EXAMPLE 10

12.1 g (50 mmoles) of 4-benzyl-6-methyl-1,3-dihydro-furo[3,4-c]pyridin-7-ol are suspended in 40 ml of dry dimethylsulfoxide and converted to the sodium salt by adding 1.75 g (60 mmoles) of sodium hydride (85% strength in oil) at 20° C. When the evolution of hydrogen has ceased, 9.25 g (100 mmoles) of epichlorohydrin are added, the mixture is heated for 1.5 hours at 60° C., 30 g (0.5 mole) of isopropylamine are added and this mixture is heated in an autoclave at 100° C. for 2.5 hours. Excess amine and dimethylsulfoxide are stripped off under reduced pressure. The residue is taken up in methylene chloride, the solution is washed with 10% strength sodium hydroxide solution and water and is dried, and the solvent is again stripped off. The residue is purified by chromatography over silica gel (using ethyl acetate and methanol). On converting the product to the hydrochloride and recrystallizing this from acetonitrile, 10.5 g of 4-benzyl-6-methyl-1,3-dihydro-furo[3,4-c]pyridin-7-yl 2-hydroxy-3-isopropylaminopropyl ether hydrochloride, of melting point 152°–154° C., are obtained.

The following compounds are prepared by methods similar to Examples 8 to 10. The melting points are those of the hydrochlorides.

11. 4-Benzyl-6-methyl-1,3-dihydro-furo[3,4-c]pyridin-7-yl 4-isopropylaminobutyl ether; melting point 198°–199° C.

12. 4-Benzyl-6-methyl-1,3-dihydro-furo[3,4-c]pyridin-7-yl 5-isopropylamino-(3-methylpentyl) ether; melting point 169°–170° C.

13. 4-Benzyl-6-methyl-1,3-dihydro-furo[3,4-c]pyridin-7-yl 5-diethylamino-(3-methylpentyl) ether; melting point 161°–162° C.

14. 4-Benzyl-6-methyl-1,3-dihydro-furo[3,4-c]pyridin-7-yl 4-tert.-butylamino-butyl ether; melting point 198°–199° C.

I claim:

1. A 4-α-amino-arylmethyl-6-methyl-1,3-dihydrofuro[3,4-c]pyridin-7-ol of the formula I

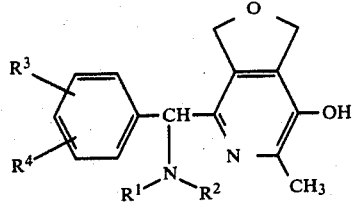

where
$R^1$ and $R^2$ together are selected from the group consisting of piperidine, 3-methylpiperidine, 4-methylpiperidine, morpholine, 3-methylmorpholine, piperazine, N-methyl-piperazine, hexamethyleneimine, pyrrolidine, 3-methylpyrrolidine, 1,3-propyleneimine and ethyleneimine, and
$R^3$ and $R^4$ are hydrogen, hydroxyl, $C_{1-3}$-alkyl, $C_{1-3}$-alkoxy or halogen.

* * * * *